United States Patent [19]
Garrett et al.

[11] Patent Number: 5,016,624
[45] Date of Patent: May 21, 1991

[54] REFORMABLE SUPPORT STRUCTURE

[76] Inventors: R. Patrick Garrett; Miles S. Krivoshia, both of 5849 Bartlett St., Pittsburgh, Pa. 15217

[21] Appl. No.: 502,976
[22] Filed: Apr. 2, 1990
[51] Int. Cl.⁵ .................. A61N 15/00; A61F 5/04
[52] U.S. Cl. ................ 128/82.1; 128/87 R; 128/89 R
[58] Field of Search ............ 128/68.1, 82.1, 87 R, 128/87 A, 87 C, 89 R, 91 R

[56] References Cited

U.S. PATENT DOCUMENTS

| | | | |
|---|---|---|---|
| 1,384,467 | 7/1921 | Homan | 128/82.1 |
| 2,434,198 | 1/1948 | Duma | 128/82.1 |
| 2,573,791 | 11/1951 | Howells | 128/82.1 |
| 2,590,212 | 3/1952 | Samuels | 128/82.1 |
| 2,675,798 | 4/1954 | Rosmarin | 128/82.1 |
| 3,326,211 | 6/1967 | Logue | 128/82.1 |
| 4,287,011 | 9/1981 | Derbsyhire | 128/82.1 |
| 4,616,629 | 10/1986 | Moore | 128/82.1 |

Primary Examiner—Robert A. Hafer
Assistant Examiner—Michael Brown
Attorney, Agent, or Firm—Ansel M. Schwartz

[57] ABSTRACT

An apparatus to conform with an object including a device for heating. The heating device is conformable. The apparatus is also formed of an element within which the heating device is in contact such that when the heating device is activated to produce heat, the element becomes conformable and when the heating device is deactivated, the element becomes rigid. In a preferred embodiment, the heating device is a heating wire which is embedded in the element and there is a housing which contains a conformable support structure in contact with the element which provides a shape to which the element can harden into after the heating device has melted the element.

6 Claims, 2 Drawing Sheets

REFORMABLE SUPPORT STRUCTURE

FIELD OF THE INVENTION

The present invention relates to supports. More specifically, the present invention relates to a conformable support that could be used as a splint.

BACKGROUND OF THE INVENTION

It is a fact that most injuries which demand immobilization for emergency transport and recuperation would benefit from the superior fit and support of a cast. Unfortunately, casts suffer several restrictive drawbacks. Casts:

are awkward and time consuming to apply
are bulky and cumbersome
offer no adjustability
must be destroyed when removed
offer poor ventilation These drawbacks incite the need for alternative immobilization devices that overcome these deficiencies. Splints are examples of immobilization devices that sacrifice both fit and support yet solve most of casts inherent drawbacks. Splints are easy to apply, adjust, remove and provide ventilation. It is this versatility that justifies their use in many medical situations.

Numerous techniques and methods have been proposed which address the need for immobilization devices that combine the advantages of both the splint and cast. Hill-Byrne, U.S. Pat. No. 4,727,865 describes a method that allows a cast to be removed. The method consists of fabricating a cast in the traditional manner, cutting the cast into two sections, attaching fasteners to their common interface and lastly assembling the unit on the injury. Hollrah U.S. Pat. No. 4,766,890, describes a cast with an underlying support structure of spaced apart ribs. These ribs from a grid that keep the cast from contacting the injury. While the former allows the cast to be removed and the latter improves ventilation, both of these methods increase the time and complexity of the casting process, thus prohibiting their use in numerous medical situations.

Larson, U.S. Pat. No. 3,580,248 describes a rigid cast-like structure that uses an inflatable liner to provide adjustability and hinges to provide ease of removal. However, the complexity of the fabrication demands that the apparatus be manufactured prior to the injury. This necessitates the injury to be immobilized in the casts predetermined orientation. This drastically lessons the methods' versatility.

Sterling, U.S. Pat. No. 4,019,504 describes a splint that is adjustable. The apparatus consists of two slats connected by a slidable pivot. Santy, U.S. Pat. No. 4,280,490 provides numerous hinges to allow the structure to be adjusted in three planes. These devices do constitute an improvement over previous splinting apparatuses, however, they still offer limited fit and immobilization.

In order to attain a high degree of fit, comfort and immobilization the apparatus must do more than adjust, it must be formable. Further, if it is to remain versatile, it must be reformable. Numerous devices have been proposed which offer reformable structures. One method present in the art is to use a malleable material to provide reformability. U.S. Pat. No. 2,506,464 pivotaly connects two strips of metal to provide four bendable legs for splinting a finger. Sheinberg, U.S. Pat. No. 3,955,565 describes a flat u-shaped strip of malleable metal that is used to sandwich injured limbs. These devices can, to some extent, be bent to fit a patient. Unfortunately, they require extensive handling and adjustment, while providing only minimal conformability. Further, the force these devices can resist cannot be greater than the force that formed them. In many instances, this force is not sufficient to offer adequate rigidity.

It would be desirable to have an immobilization device that is easily conformable yet structurally rigid. These conflicting requirements impel the need for a structure that has two states, conformable and rigid. Several structures have been proposed that offer this dual-state characteristic. Seeler, U.S. Pat. No. 4,508,112 describes a fluid pressure actuated immobilizing structure. The device consists of two flexible and coaxial tubes. The inner tube expands under fluid pressure and exerts a force on the outer tube which rigidizes the structure. Unfortunately, this device is awkward to apply, is excessively bulky and requires a pressure source. Wirtz, U.S. Pat. No. 4,657,003 describes an immobilizing device that consists of polystyrene beads contained in an evacuable plastic bag. After the bag is placed around the injury, a vacuum source is used to evacuate the bag. This causes the beads to compress. The frictional force created allows the device to form a semi-rigid structure. Since the maximum pressure available to compact these beads is only atmospheric, these devices cannot be used when significant structural support is needed. Also, this device is necessarily bulky.

Materials such as those described in U.S. Pat. Nos. 4,483,333 and 4,600,618 are a type of material that are used extensively to provide a dual-state structure. These low temperature thermoforming plastic materials are reformable at raised temperatures below their curing point and are structurally rigid at normal ambient temperature. Their most restrictive drawback is that an external heating source must be readily available. Another problem is the time and complexity needed to fabricate such a device. Groiso, U.S. Pat. No. 4,852,556 addresses these problems by offering a pre-made support structure that is stored in a sterilized bag filled with water. Though Groiso was successful at minimizing the time and complexity of fabrication, a heating source must be available to heat the hot water. Since hot water is the preferred heating means, readjustment of the structure entails removal of the apparatus from the injury, in order to reheat the thermo plastic material. Further, since the apparatus must be removed when it is structurally rigid, it cannot encircle the injury. This limits its immobilization and rigidity.

The patents cited above all offer solutions to particular insufficiencies inherent to immobilization and support structures. Some have solved one problem by creating another. While others have attained varying degrees of success in providing a versatile immobilizing-/support device.

It is a principle objective of the invention to describe a general support structure that can be used in any situation that requires structural support and reformability.

A second objective of the present invention is to provide a dual-state support structure that could be used to provide superior immobilization and versatility for supporting portions of the human body with no significant drawbacks.

SUMMARY OF THE INVENTION

The present invention pertains to an apparatus to conform with an object. The apparatus comprises means for heating. The heating means is conformable. The apparatus is also comprised of an element within which the heating means is disposed such that when the heating means is activated to produce heat, the element becomes conformable and when the heating means is deactivated, the element becomes rigid. In a preferred embodiment, the heating means is a heating wire which is embedded in a material and there is a housing which contains a conformable structure which is reformable at a raised temperature below the curing temperature of the said material and which is structurally stable at normal ambient temperatures in contact with the element which provides a shape to which the element can harden into after the heating means has made the element conformable.

BRIEF DESCRIPTION OF THE DRAWINGS

In the accompanying drawings, the preferred embodiments of the invention and preferred methods of practicing the invention are illustrated in which.

DESCRIPTION OF THE PREFERRED EMBODIMENT

Figure 1:
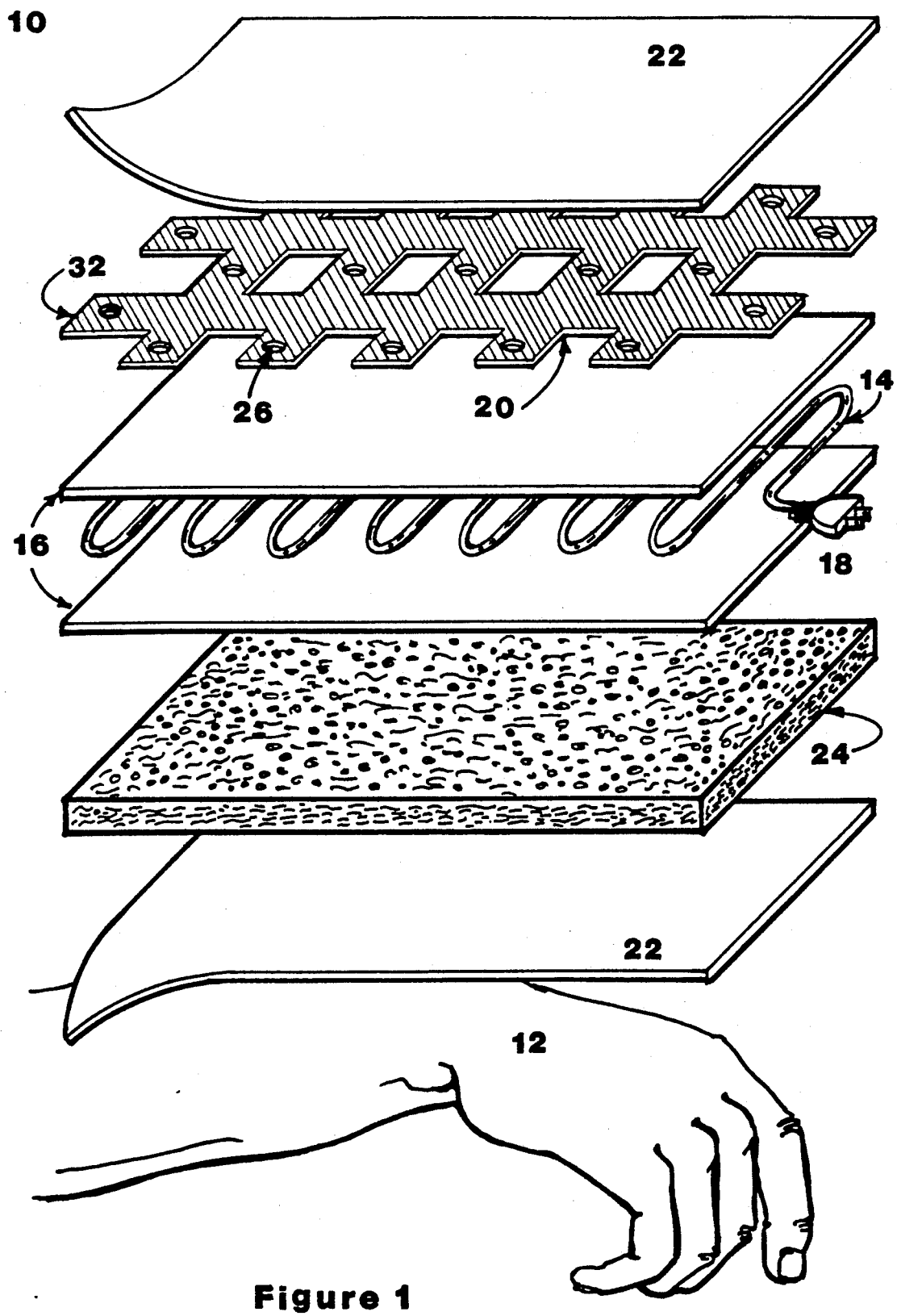
FIG. 1 is a schematic representation of an exploded view of an apparatus to conform with an object.

Referring now to the drawings wherein like reference numerals refer to similar or identical parts throughout the several views and more specifically to FIG. 1 thereof, there is shown a schematic representation of an exploded view of an apparatus 10 to conform with an object 12, such as a limb. The apparatus 10 is comprised of means 14 for heating. The heating means 14 is also conformable. The apparatus 10 is also comprised of an element 16 within which the heating means 14 is disposed such that when the heating means 14 is activated to produce heat, the element 16 becomes conformable, and when the heating means 14 is deactivated, the element 16 becomes rigid. Preferably, the heating means 14 is a heating wire which, for instance, can have an electric plug 18 extending out of the element 16. The heating wire is preferably embedded in the element 16. The material the element 16 is made out of is a thermoplastic which is moldable at temperatures greater than 110°.

The apparatus 10 can also include a conformable support structure 20 in contact with the element 16. The support structure 20 provides a shape to which the element 16 can harden into after the heating means 14 has melted the element 16. Preferably, the support structure 20 is made out of malleable material such as aluminum and is thin enough and cut in such a way as to provide the desired support yet also the desired conformability. The support structure 20 preferably has holes 26 through which the element 16 bonds to the support structure 20.

The apparatus 10 can additionally include a housing 22 which contains the support structure 20, the element 16 and the heating means 14. The housing 22 preferably is made out of vinyl. There can also be a cushion 24 disposed in the housing 22 between the element 16 and the housing 22.

Figure 2:
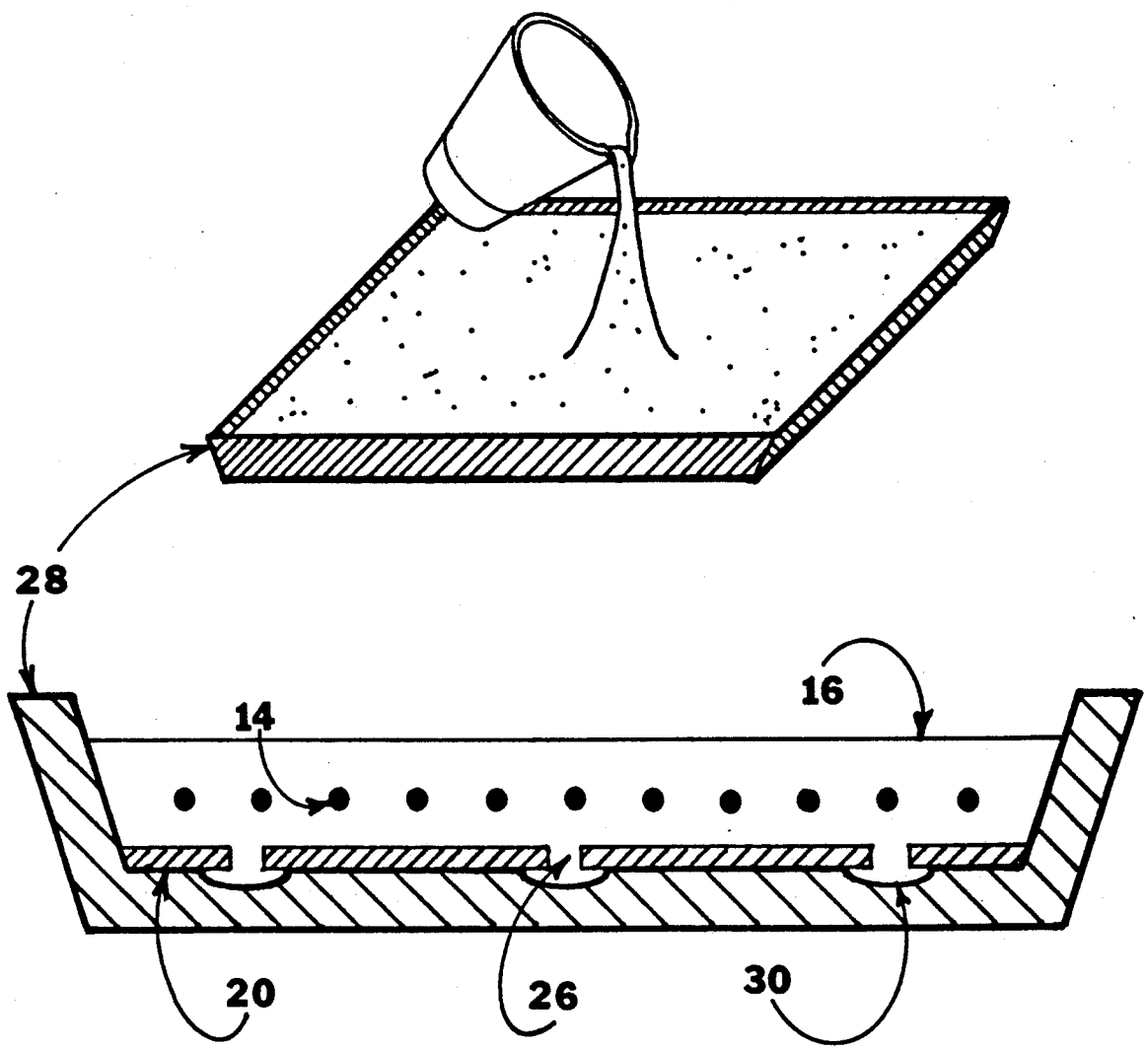
FIG. 2 is schematic representation of a partial cross sectional view of the apparatus.

The apparatus 10 is preferably formed by placing the support structure 20 into a mold 28 as shown in FIG. 2. A thermoplastic material such as described in Aquaplast ® U.S. Pat. No. 4,483,333 (polyepsiloncaprolactone), which has been heated to a liquid state is then poured into the mold 28 to cover the support structure 20. Polyepsiloncaprolactone is a material whose molecules become cross-linked subject to electron radiation. It should be noted that any thermoplastic material whose molecules can be cross-linked can be used as the element 16. The heating means 14 is then placed into the mold 28 atop the support structure 20 and into the liquid polymer covering the support structure 20. After the heating means 14 is in place in the mold 28, more liquid polymer is poured into the mold until the predetermined amount fills the mold 28 covering the heating means 14 and support structure 20. Before the liquid polymer cools, it seeps through the holes 26 in the support structure 20. When the liquid polymer cools and solidifies, the polymer then has seeped through the holes 26 forming nibs 30 which aid in the bonding of the support structure 20 to the solidified liquid polymer which forms the element 16. Finally, as in Aquaplast ® U.S. Pat. No. 4,483,333, the molecules of the thermoplastic material are cross-linked by any preference means, such as radiation, thereby forming an elastic mesh functioning to restrict movement of the heating means 14 and support structure 20 within the element 16 of thermoplastic material.

In the operation of the preferred embodiment, the apparatus 10 is used as a splint for an injured arm. In preparation of placing the splint on the injured arm, the electric plug 18 that is connected to the heating wire disposed in the element 16 is connected to an electric source (not shown). Through ohmic heating in the heating wire, the element 16 is melted. The time for melting is on the order of a few minutes. Once the element 16 is melted, the apparatus 10 is placed on the arm and molded thereto. This is done by gently pressing on the apparatus 10 since the aluminum support structure 20 is thin enough that it can be bent and has slats 32 which facilitate the bending of the support structure 20. The housing 22 made of vinyl contains the element 16 heating wire and support structure 20 therein as well as the cushion 24 which is between the vinyl covering of the housing 22 and the element 16. The cushion 24 provides some degree of comfort and also some degree of thermal insulation from the more conformable element 16 with respect to the arm of a user. After the element 16 is made conformable, the electric plug 18 is disconnected from the electric source so that the conformable element 16 can begin to cool and solidify. The conformable element 16, as it solidifies, takes on the shape of the aluminum support structure 20 and upon complete solidification, provides a rigid splint that conforms to the injured arm.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. An improved method of forming a reformable structure comprising the steps of:

orienting flexible heating means within a mold;

heating thermoplastic material which becomes formable at temperatures less than 200° F. to a liquid state; and introducing the thermoplastic material into said mold and around said flexible heating means.

2. A method as described in claim 1 including the additional step, after the introducing step, the step of cross-linking the molecules of said thermoplastic material thereby forming an elastic mesh of cross-linked thermoplastic molecules functioning to restrict movement of the heating means within the thermoplastic material.

3. A method as described in claim 2 wherein the thermoplastic material is polyepsiloncaprolactone.

4. A method as described in claim 15 wherein the flexible heating means is a heating wire.

5. A method as described in claim 1 including the additional step of orienting a conformable support structure within said mold prior to the step of introducing said thermoplastic material, said support structure supporting said thermoplastic material while it is in a softened state due to the heating effect of said flexible heating means.

6. A method as described in claim 5 wherein the flexible heating means is a heating wire.

* * * * *